United States Patent
Lin et al.

(10) Patent No.: US 10,980,611 B2
(45) Date of Patent: Apr. 20, 2021

(54) RADIOPAQUE STRUCTURE AND IMPLANTED MEDICAL DEVICE HAVING RADIOPAQUE STRUCTURE

(71) Applicant: Biotyx Medical (Shenzhen) Co., Ltd., Shenzhen (CN)

(72) Inventors: Wenjiao Lin, Shenzhen (CN); Li Qin, Shenzhen (CN)

(73) Assignee: Biotyx Medical (Shenzhen) Co., Ltd., Shenzhen (CN)

( * ) Notice: Subject to any disclaimer, the term of this patent is extended or adjusted under 35 U.S.C. 154(b) by 407 days.

(21) Appl. No.: 15/778,032

(22) PCT Filed: Jun. 14, 2016

(86) PCT No.: PCT/CN2016/085648
§ 371 (c)(1),
(2) Date: May 22, 2018

(87) PCT Pub. No.: WO2017/107404
PCT Pub. Date: Jun. 29, 2017

(65) Prior Publication Data
US 2018/0333219 A1  Nov. 22, 2018

(30) Foreign Application Priority Data
Dec. 25, 2015  (CN) .......................... 201510996110.2

(51) Int. Cl.
*A61B 90/00* (2016.01)
*A61L 31/18* (2006.01)
(Continued)

(52) U.S. Cl.
CPC .............. *A61B 90/39* (2016.02); *A61B 90/00* (2016.02); *A61F 2/82* (2013.01); *A61L 29/18* (2013.01);
(Continued)

(58) Field of Classification Search
CPC . A61B 90/00; A61B 90/39; A61B 2090/3966; A61B 2090/3904–3916;
(Continued)

(56) References Cited

U.S. PATENT DOCUMENTS 4,503,169 A * 3/1985 Randklev ............... A61K 6/887
523/117
4,776,337 A * 10/1988 Palmaz ................... A61F 2/915
623/1.11

(Continued)

FOREIGN PATENT DOCUMENTS

| CN | 101652151 A | 2/2010 |
| CN | 102000364 A | 4/2011 |

(Continued)

OTHER PUBLICATIONS

Chinese Office Action dated Oct. 26, 2018, in connection with corresponding CN Application No. 201510996110.2 (10 pgs., English translation not available).

(Continued)

*Primary Examiner* — Oommen Jacob
(74) *Attorney, Agent, or Firm* — Maier & Maier, PLLC

(57) ABSTRACT

A radiopaque structure and an implanted medical instrument having the radiopaque structure. The radiopaque structure includes at least one radiopaque unit, and each radiopaque unit includes at least one radiopaque object. In at least one incidence direction of a light source, all the radiopaque objects in the radiopaque structure are divided into n regions according to the thickness in the incidence direction, and a projection area Sm of m regions of the n regions and an effective thickness dm of the m regions meet Sm−0.0136 (dm)a≥0, wherein −0.95≤a≤−0.85 and 1≤m≤n. The radiopaque structure has good or excellent visibility.

20 Claims, 2 Drawing Sheets

(51) Int. Cl.
*A61L 29/18* (2006.01)
*A61F 2/82* (2013.01)
*A61L 31/02* (2006.01)

(52) U.S. Cl.
CPC ............ *A61L 31/022* (2013.01); *A61L 31/18* (2013.01); *A61B 2090/3904* (2016.02); *A61B 2090/3937* (2016.02); *A61B 2090/3966* (2016.02); *A61F 2210/0004* (2013.01); *A61F 2250/0032* (2013.01); *A61F 2250/0098* (2013.01)

(58) Field of Classification Search
CPC ......... A61B 2090/392; A61B 2090/3937–395; A61B 2090/3954; A61L 29/18; A61L 31/18; A61L 31/022; A61F 2/82; A61F 2250/0032; A61F 2210/0004; A61F 2250/0098; C09K 11/00–025; C09K 11/04; C09K 11/06–07; C09K 11/08
See application file for complete search history.

(56) References Cited

U.S. PATENT DOCUMENTS

| | | | | |
|---|---|---|---|---|
| 6,355,058 | B1* | 3/2002 | Pacetti | A61L 29/18 |
| | | | | 427/2.25 |
| 6,540,721 | B1 | 4/2003 | Voyles et al. | |
| 8,535,370 | B1* | 9/2013 | Eckert | A61F 2/07 |
| | | | | 623/1.34 |
| 9,119,641 | B2* | 9/2015 | Windolf | A61B 90/10 |
| 2001/0021873 | A1* | 9/2001 | Stinson | A61F 2/90 |
| | | | | 623/1.34 |
| 2005/0065434 | A1* | 3/2005 | Bavaro | A61B 90/39 |
| | | | | 600/424 |
| 2005/0078802 | A1* | 4/2005 | Lang | G06T 7/80 |
| | | | | 378/207 |
| 2006/0293581 | A1* | 12/2006 | Plewes | A61K 49/0419 |
| | | | | 600/407 |
| 2007/0250158 | A1* | 10/2007 | Krivoruchko | A61L 31/082 |
| | | | | 623/1.44 |
| 2008/0058919 | A1* | 3/2008 | Kramer-Brown | A61L 31/16 |
| | | | | 623/1.34 |
| 2009/0264990 | A1* | 10/2009 | Bruszewski | A61F 2/07 |
| | | | | 623/1.34 |
| 2010/0131044 | A1* | 5/2010 | Patel | A61F 2/915 |
| | | | | 623/1.16 |
| 2011/0166447 | A1* | 7/2011 | Windolf | A61B 90/10 |
| | | | | 600/426 |
| 2011/0306867 | A1* | 12/2011 | Gopinathan | A61B 5/064 |
| | | | | 600/407 |
| 2014/0222093 | A1* | 8/2014 | Mafi | A61B 17/8855 |
| | | | | 606/86 R |
| 2015/0063539 | A1* | 3/2015 | Hayler | G21K 1/10 |
| | | | | 378/57 |
| 2016/0200970 | A1* | 7/2016 | Sakurai | A61B 90/39 |
| | | | | 252/478 |
| 2016/0242849 | A9* | 8/2016 | Crawford | A61B 34/10 |
| 2018/0333219 | A1* | 11/2018 | Lin | A61L 29/18 |

FOREIGN PATENT DOCUMENTS

| | | |
|---|---|---|
| CN | 102448380 A | 5/2012 |
| CN | 204744108 U | 11/2015 |
| EP | 0987042 A2 | 3/2000 |
| WO | 01/49340 A1 | 7/2001 |

OTHER PUBLICATIONS

International Search Report dated Sep. 23, 2016 of corresponding International Application No. PCT/CN2016/085648; 7 pgs.

* cited by examiner

RADIOPAQUE STRUCTURE AND IMPLANTED MEDICAL DEVICE HAVING RADIOPAQUE STRUCTURE

FIELD

The present application relates to a radiopaque structure, and more particularly relates to a radiopaque structure used for an implanted medical device and the implanted medical device having the radiopaque structure.

BACKGROUND

Interventional radiology, also called interventional therapeutics, is an emerging discipline that has been developed rapidly in recent years and integrates imaging diagnosis and clinical therapy. The interventional radiology is a general term of a series of technologies of leading a specific implanted device (hereinafter referred to as "implant") into a diseased portion of human body through a natural orifice or a tiny wound of the human body for minimally invasive therapy with a puncture needle, a catheter and other intervention equipment under the guide and monitoring of imaging equipment such as Digital Subtraction Angiography (DSA), Computed Tomography (CT), ultrasound and magnetic resonance. The existing implant substrate are made of metal-based and non-metal-based materials, such as non-absorbable metal materials: stainless steel, a nickel-titanium alloy, a cobalt-chromium alloy and the like, or absorbable metal materials: a magnesium base, an iron base, a zinc base and the like, and degradable polymer-based materials such as polylactic acid, polycaprolactone or its copolymer and a blend.

When the radiation density of the material of the implant substrate is greater than the density of a human tissue or organ around an implanted position, a contrast image may be formed for diagnosis or clinical treatment via X-ray irradiation. A implant with a certain thickness made of the stainless steel, the nickel-titanium alloy or the cobalt-chromium alloy, has a relatively high radiation density, and may have relatively high X-ray radiopacity after being implanted. For example, a stainless steel vascular stent with a thickness more than 80 microns may form a distinct image by itself in the medical imaging equipment DSA, so that the position and the shape may be easily identified, or the stent has good visibility, wherein the thickness is the wall thickness of the implant.

For a vascular stent, the smaller the thickness, the better fitting with the blood vessel wall, thus lower shear interference of a stent strut to blood flow in a blood vessel would be caused, which is more favorable for avoiding thrombosis. Therefore, for a medical application, it tends to adopt a relatively thin vascular stent. However, when the thickness of the stainless steel stent is less than 70 microns, the image of the stent displayed under the DSA equipment is not clear enough, and the position and the shape of the stent are hard to visually identify, so that it is necessary to improve the visibility.

As the density of an implant made of the magnesium-based alloy and a polymer such as polylactic acid, polycaprolactone or its copolymer, and the like is very low, the obtained implant may have thickness reaching the hundred-micron level, but its visibility under the DSA equipment in the prior art is still very poor. For example, a vascular stent which is made of the polymer and has the wall thickness of 120 to 220 microns is nearly invisible in the medical imaging equipment DSA, which leads to a fact that a doctor cannot accurately position the stent in a surgical procedure.

Therefore, for a polymer-based implant with extremely poor visibility, as well as a relatively thin metal-based implant, it is necessary to dispose an extra radiopaque structure at a proper position on the implant and enable the radiopaque structure to be identified by the doctor under the DSA to assist the doctor in accurately positioning the implant.

Generally, it is desirable that the smaller the size of the radiopaque structure the better to avoid the influence on the design and the relevant mechanical property of the implant. However, if the size of the radiopaque structure is not properly set, particularly when the adoption of the radiopaque structure with a relatively small thickness (20 to 100 microns) is the only option because of the limit of designs of some thin-wall implants (20 to 70 microns), the extremely small size of the radiopaque structure may cause poor visibility, and the aim of assisting in judging the position and the shape of the implant may not be achieved.

Summary

In view of this, it is necessary to provide a radiopaque structure having good or excellent visibility and an implanted medical device having the radiopaque structure to overcome the above-mentioned shortcomings.

The present application provides a radiopaque structure, including at least one radiopaque unit. Each radiopaque unit includes at least one radiopaque object; in at least one incidence direction of a light source, all the radiopaque objects in the radiopaque structure are divided into n regions according to the thickness in the incidence direction; a projection area $S_m$ of m regions of the n regions and the effective thickness $d_m$ of the m regions accord with $S_m - 0.0136(d_m)^a \geq 0$, where a is more than or equal to $-0.95$ and less than or equal to $-0.85$, and m is more than or equal to 1 and less than or equal to n.

In one embodiment, a is equal to $-0.90$.

In one embodiment, in the incidence direction, the effective thickness $d_m$ of the m regions of the n regions ranges from 0.02 mm to 0.24 mm.

In one embodiment, in the incidence direction, the effective thickness $d_m$ of the m regions of the n regions ranges from 0.02 mm to 0.1 mm.

In one embodiment, in the incidence direction, the projection area $S_m$ of the m regions of the n regions is less than or equal to 1 $mm^2$.

In one embodiment, in the incidence direction, the projection area $S_m$ of the m regions of the n regions is less than or equal to 0.5 $mm^2$.

In one embodiment, the radiopaque structure only includes one radiopaque unit, and the radiopaque unit includes at least one radiopaque object.

In one embodiment, the radiopaque unit includes multiple mutually spaced radiopaque objects.

In one embodiment, the radiopaque structure includes multiple mutually spaced radiopaque units, and each radiopaque unit includes at least one radiopaque object.

In one embodiment, each radiopaque unit includes multiple mutually spaced radiopaque objects.

In one embodiment, the radiopaque object is only made of a radiopaque material, and the radiopaque material is selected from the group consisting of gold, platinum, osmium, rhenium, tungsten, iridium, rhodium, tantalum, barium sulfate, columbium sesquioxide, titanium oxide, zirconium oxide, elemental iodine and iodide.

In one embodiment, when the radiopaque object includes various radiopaque materials, the average atomic number of a mixture of the various radiopaque materials is less than the atomic number of gold.

In one embodiment, the radiopaque object includes a radiopaque material and a non-radiopaque material, and the radiopaque material is selected from the group consisting of gold, platinum, osmium, rhenium, tungsten, iridium, rhodium, tantalum, barium sulfate, columbium sesquioxide, titanium oxide, zirconium oxide, elemental iodine and iodide.

In one embodiment, the non-radiopaque material is a degradable polymer material.

The present application further provides an implanted medical device, including a substrate and at least one radiopaque structure which is mentioned in any item above and is connected with the substrate.

In one embodiment, there are multiple radiopaque units, and the radiopaque objects of at least two radiopaque units have an overlapping region in the incidence direction.

In one embodiment, there are multiple radiopaque structures, wherein at least one radiopaque structure includes multiple mutually spaced radiopaque units, and each radiopaque unit in the radiopaque structure includes multiple mutually spaced radiopaque objects; and at least another one radiopaque structure includes one radiopaque unit which includes multiple mutually spaced radiopaque objects.

In one embodiment, the substrate is a metal having a thickness less than or equal to 150 microns, or a polymer having a thickness less than or equal to 220 microns.

In one embodiment, the substrate is a magnesium-based alloy having a thickness less than or equal to 150 microns.

In one embodiment, the substrate is a zinc-based alloy having a thickness less than or equal to 100 microns.

In one embodiment, the substrate is an iron-based alloy having a thickness less than or equal to 70 microns.

According to the radiopaque structure and the implanted medical device including the radiopaque structure of the present application, in at least one incidence direction of the light source, at least one group of the projection area $S_m$ and the effective thickness $d_m$ of all the radiopaque objects in the radiopaque structure accords with $S_m - 0.0136(d_m)^a \geq 0$, so that the radiopaque structure has good or excellent visibility.

BRIEF DESCRIPTION OF THE DRAWINGS

A further description will be made to the present application in combination with accompanying drawings and embodiments as follows. In drawings.

DETAILED DESCRIPTION

For the purpose of making the technical features, objectives and effects of the present application more clear, a detailed description will be made to specific implementation modes of the present application in conjunction with the drawings.

Unless otherwise specified, all technical and scientific terms used herein are the same as meanings of general understandings of persons skilled in the art. The terms used in the description herein are merely used to describe objectives of specific embodiments, bur not intended to limit the present application.

The visibility of the present application may be measured under a CGO-2100C type medical angiography X-ray machine produced by China Resources Wandong Medical Equipment Co., Ltd., and X-ray pulse prospective imaging parameters are selected as follows: ultrashort pulse (6 to 30 frames/second), tube pressure of 65 to 100 kV and current of 400 to 600 mA. These parameters all represent a general technical level of the current angiography. In order to reduce the radiation dosage to a patient and a surgeon, on the premise of not affecting the image quality, such parameter settings as high voltage, low current and low frame frequency are generally used as far as possible.

Figure 1:
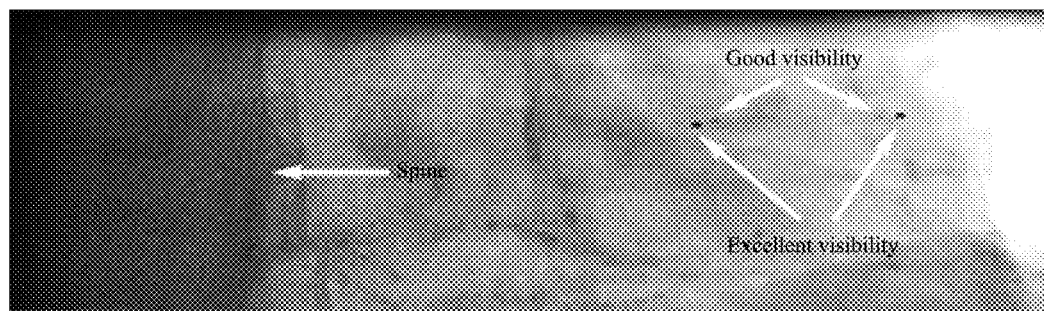
FIG. 1 is a DSA image of a radiopaque—structure in an implant.

As shown in FIG. 1, the visibility of a radiopaque structure in an implant under imaging equipment may be judged according to an image formed by the radiopaque structure under the imaging equipment. When an infill and a boundary of the image are relatively fuzzy, but the position and the shape still may be visually identified with eyes alone, the visibility is good; and when the infill and the boundary of the image are very clear, and the position and the shape may be easily visually identified with the eyes alone, the visibility is excellent.

The radiopaque structure of the present application only represents a radiopaque structure having good or excellent visibility, and includes at least one radiopaque unit, and each radiopaque unit includes at least one radiopaque object. The radiopaque unit is a set of the radiopaque objects cooperating to form one visible image. The radiopaque structure of the present application may only include one radiopaque unit, and the radiopaque unit only includes one integral radiopaque object. In at least one incidence direction of a light source, the radiopaque object may form one integral image with good or excellent visibility. Or the radiopaque structure may only include one radiopaque unit, and the radiopaque unit includes multiple mutually spaced radiopaque objects. In at least one incidence direction of the light source, the multiple mutually spaced radiopaque objects may form one integral image with good or excellent visibility. Or the radiopaque structure includes multiple mutually spaced radiopaque units, and each radiopaque unit includes at least one radiopaque object. In at least one incidence direction of the light source, all the radiopaque objects included in the multiple mutually spaced radiopaque units may form one integral image with good or excellent visibility. When the radiopaque unit includes multiple radiopaque objects, it may include a radiopaque object which is invisible by itself, but is visible after cooperating with other radiopaque objects, namely the radiopaque object which contributes to the visibility of a finally observed image, or it may also include a radiopaque object which is invisible by itself and may not contribute to the visibility of the finally observed image after cooperating with other radiopaque objects.

No matter what a specific composition of the radiopaque structure is, the radiopaque structure may form an intact, continuous and independent image with good or excellent visibility under the imaging equipment. The image may be of a point shape, a ball shape, an opened line shape or a closed line shape.

It should be understood that the radiopaque objects may be integral radiopaque wires, radiopaque rings or radiopaque blocks and the like, and may be directly twined on the surface of an implanted medical device or embedded into grooves in the surface of the implanted medical device, or also fill open holes in the implanted medical device.

The visibility of the radiopaque structure under the imaging equipment depends on two influence factors: the radiation impenetrability of the radiopaque object in the radiopaque structure and the detectability of the radiopaque structure.

The radiation impenetrability of the radiopaque object is determined according to the ratio of the emergence intensity of the light source to the incidence intensity. As shown in FORMULA (1):

$$I = I_0 \cdot exp(-\mu d) \quad (\text{FORMULA 1})$$

where I is the emergence intensity of the light source penetrating through the radiopaque object;

$I_0$ is the incidence intensity of the light source incident to the surface of the radiopaque object;

u is a linear attenuation coefficient of the radiopaque object, which is not a constant, and its physical significance is a relative attenuation amount or attenuation percentage of the light source intensity when the light source penetrates through a unit substance thickness; and d is the thickness of the radiopaque object along the incidence direction of the light source. $I/I_0$ is the ratio of the emergence intensity of the light source penetrating through the radiopaque object to the incidence intensity. Smaller $I/I_0$ shows higher radiation impenetrability of the radiopaque object. Therefore, under the light source with the same incidence intensity, the radiation impenetrability of the radiopaque object is in direct proportion to the linear attenuation coefficient u of the radiopaque object and the thickness d of the radiopaque object along the incidence direction of the light source, that is, if the linear attenuation coefficient u and the thickness d of the radiopaque object are greater, its radiation impenetrability is higher, but the linear attenuation coefficient u of the radiopaque object is related to the atomic number of the radiopaque object: the greater the atomic number of the radiopaque object, the greater its linear attenuation coefficient u. That is, if the atomic number of the radiopaque object and the thickness along the incidence direction of the light source are greater, its radiation impenetrability is higher.

The detectability of the radiopaque structure jointly depends on imaging equipment, the visual resolution and the projection area of all the radiopaque objects in the radiopaque structure in the incidence direction of the light source. Under the condition that the imaging equipment and the visual resolution are confirmed, the detectability of the radiopaque structure depends on the projection area of all the radiopaque objects in the radiopaque structure along the incidence direction of the light source.

It should be noted that for the same radiopaque structure, when the incident directions of the light source are different, the projection areas of all the radiopaque objects of the radiopaque structure may be possibly different, and correspondingly, images formed by the radiopaque structure in different incidence directions of the light source also may be different. For example, the radiopaque structure includes one straight-line segment radiopaque object. When the incidence direction of the light source is parallel to a lengthwise direction of the straight-line segment, the formed image is a point; and when the incidence direction of the light source is perpendicular to the lengthwise direction of the straight-line segment, the formed image is a straight-line segment.

It can be known from the visibility analysis for the radiopaque structure under the imaging equipment that the visibility of the radiopaque structure is related to the atomic number of the radiopaque object and the projection area and the thickness of the radiopaque object in the incidence direction of the light source.

A radiopaque object material is generally a heavy metal which is selected from at least one of or an alloy of gold, platinum, osmium, rhenium, tungsten, iridium, rhodium or tantalum and the like. The radiopaque object material also may be a metal compound such as barium sulfate, columbium sesquioxide, titanium oxide or zirconium oxide, or further may be a non-metal such as elemental iodine or iodide. Different radiopaque object materials have different atomic numbers.

In the present application, in a certain incidence direction of the light source, all the radiopaque objects of the radiopaque structure are divided into n regions (n is more than or equal to 1) according to their thicknesses in the incidence direction. It should be understood that the thicknesses of the n regions may be different from one another, or partially equal, or totally equal. When n is more than or equal to 2, the thicknesses of the radiopaque objects in each region may be equal to or different from those of the radiopaque objects in other regions; and when n is equal to 1, it means that the thicknesses of all the radiopaque objects are equal. It should be understood that when the radiopaque structure includes one radiopaque object, the radiopaque object is directly divided into n regions according to its thickness in the incidence direction, and each region has a projection area in the incidence direction. When the radiopaque structure includes multiple mutually spaced radiopaque objects which are not overlapped in the incidence direction, the radiopaque objects are directly divided into n regions according to their thicknesses in the incidence direction, and the projection area of the n regions in the incidence direction is equal to a sum of the projection areas of each region of the n regions in the incidence direction. When the radiopaque structure includes multiple mutually spaced radiopaque objects which are overlapped in the incidence direction, the thickness of the radiopaque object overlapping region in the incidence direction shall be a sum of the thicknesses of each radiopaque objects in the overlapping region, so that before the thicknesses of the multiple radiopaque objects are divided into n regions in the incidence direction, the thicknesses of all the radiopaque objects in the overlapping region should be summed up and deemed as an overall thickness, and for the projection area of the thickness region subjected to overlapping processing in the incidence direction, the projection area of each radiopaque object in the overlapping region is only calculated once.

M regions are taken from the n regions randomly, where m is more than or equal to 1 and less than or equal to n. For each of the m regions in the incidence direction, the projection area is $S_i$, and the thickness is $d_i$, where i is more than or equal to 1 and less than or equal to m. It should be understood that the projection area $S_m$ of the m regions is a sum of the projection areas $S_i$ of the respective m regions in the incidence direction of the light source, namely $S_m = \Sigma_{i=1}^{m} S_i$. It is defined that an average thickness corresponding to the projection area $S_m$ is the effective thickness $d_m$, $d_m = (\Sigma_{i=1}^{m} S_i d_i)/S_m$. There are $C_n^m$ methods for randomly taking the m regions from the n regions, so that there are $C_n^m$ groups of $(d_m, S_m)$ values for any m regions.

For any m regions in the n regions formed by dividing all the radiopaque objects—of the radiopaque structure in a certain incidence direction of the light source, the sum of the projection areas $S_m$ and the effective thickness $d_m$ in the incidence direction may be calculated by using three-dimensional model processing software after the radiopaque structure is subjected to three-dimensional reconstruction with Micro-CT.

In the present application, the radiopaque structure accords with the condition that in at least one incidence direction of the light source, at least one group of effective thickness $d_m$ and projection area $S_m$ of all the—radiopaque objects in the radiopaque structure accords with $S_m-0.0136(d_m)^a \geq 0$ where a is more than or equal to $-0.95$ and less than or equal to $-0.85$. To be more specific, only if a is one value more than or equal to $-0.95$ and less than or equal to $-0.85$, at least one group of effective thickness $d_m$ and projection area $S_m$ of all the radiopaque objects in the radiopaque structure may accords with $S_m-0.0136(d_m)^a \geq 0'$. At the moment, the radiopaque structure has good or excellent visibility.

Figure 2:
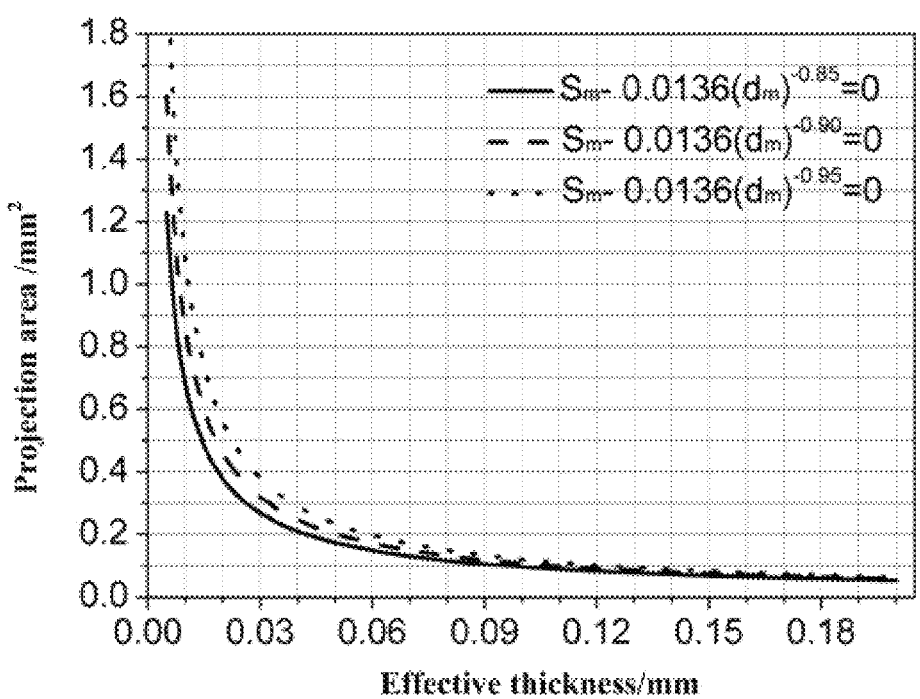
FIG. 2 is a coordinate diagram of the visibility of a radiopaque structure of the present application and the effective thickness and the projection area of radiopaque objects in the radiopaque structure.

With reference to FIG. 2, visibility curves under conditions of $S_m-0.0136(d_m)^{-0.85'}=0$, $S_m-0.0136(d_m)^{-0.90'}=0$ and $S_m-0.0136(d_m)^{-0.95'}=0$ are shown respectively. The radiopaque structures corresponding to the curves have good visibility. It can be known according to mathematics that radiopaque structures corresponding to points located in regions above the visibility curves also have good or excellent visibility, and radiopaque structures corresponding to points located in regions below the visibility curves have poor visibility.

In the present application, the regions above the visibility curves are regions where results are more than 0 after $S_m$ and $d_m$ are substituted into $S_m-0.0136(d_m)^a$ (where a is more than or equal to $-0.95$ and less than or equal to $-0.85$). Similarly, the regions below the visibility curves are regions where results are less than 0 after $S_m$ and $d_m$ are substituted into $S_m-0.0136(d_m)^a$ (where a is more than or equal to $-0.95$ and less than or equal to $-0.85$).

It should be noted that in the existing radiopaque materials, the atomic number of gold is the greatest, so that on the premise of the same thickness, the gold has the highest radiation impenetrability. It should be understood that the radiopaque object of the radiopaque structure may be prepared by mixing various radiopaque materials, so that the average atomic number of a mixture of the various radiopaque materials is less than the atomic number of the gold, that is, the radiation impenetrability of the mixture of the various radiopaque materials is lower than that of the only gold serving as the radiopaque material. Therefore, in the incidence direction of same X-ray, in order to obtain the same visibility as that of the radiopaque structure only taking the gold as the radiopaque object, the projection area $S_m$ and/or the effective thickness $d_m$ of the radiopaque object prepared by mixing the various radiopaque materials may be increased relative to the projection area $S_m$ and/or the effective thickness $d_m$ of the gold serving as the radiopaque object, that is, the result obtained by substituting the projection area $S_m$ and the effective thickness $d_m$ of the radiopaque object prepared by mixing the various radiopaque materials into the $S_m-0.0136(d_m)^a$ (where a is more than or equal to $-0.95$ and less than or equal to $-0.85$) should be more than 0.

It should be understood that the radiopaque object of the radiopaque structure also may be prepared by mixing a radiopaque material with a non-radiopaque material, for example, the radiopaque object may be prepared by mixing the radiopaque material with a polymer. The polymer may be a degradable polymer selected from polylactic acid, polylactic acid-glycolic acid, poly-glycolide lactide and the like. The volume fraction of the radiopaque material in the radiopaque object is more than 0 percent and less than 100 percent. When the radiopaque material is mixed with the non-radiopaque material according to certain volume fraction in the radiopaque object, the effective thickness $d_m$ of the radiopaque object in the incidence direction of the light source is a product of the volume fraction of the radiopaque material in the radiopaque object and the average thickness of the radiopaque object. When the effective thickness $d_m$ and the projection area $S_m$ of the radiopaque object prepared by mixing the radiopaque material and the non-radiopaque material in at least one incidence direction of the light source accord with $S_m-0.0136(d_m)^a \geq 0$, where a is more than or equal to $-0.95$ and less than or equal to $-0.85$, the radiopaque structure has good or excellent visibility.

The present application further provides an implanted medical device. The implanted medical device includes a substrate and at least one of the above radiopaque structures connected with the substrate. The substrate may be one or several of an iron-based alloy, a magnesium-based alloy, a zinc-based alloy, an absorbable polymer, stainless steel, a nickel-titanium alloy and a cobalt-chromium alloy. The iron-based alloy substrate may be pure iron or an iron-based alloy with carbon content less than or equal to 2.11 weight percent, for example, a product obtained by nitriding and/or carburizing the pure iron. The implanted medical device may be a cardiovascular stent, a cerebrovascular stent, a peripheral vascular stent, a non-vascular stent, a spring ring, an occluder or a vena cava filter, an internal fixation implant such as a bone nail, a bone lamella, an intramedullary needle or a suture, and some other small-sized implanted devices. When the substrate is a metal material, its thickness may be less than or equal to 150 microns, and further, the substrate may be a magnesium-based alloy having the thickness less than or equal to 150 microns, or a zinc-based alloy having the thickness less than or equal to 100 microns, or an iron-based alloy having the thickness less than or equal to 70 microns. When the substrate is a polymer, its thickness may be less than or equal to 220 microns. The radiopaque structure may be directly embedded into the substrate in a way of perforating the substrate, or twisted on the surface of the substrate, or partially embedded into the substrate and partially protruding from the surface of the substrate, and also may be connected with the substrate through other auxiliary members. It is worth mentioning that when the device, such as a tubular vascular stent, includes a cavity, the thickness is the wall thickness, and the substrate structure may be disposed on a connection member of two adjacent circles of waveform ring-like objects connected with the stent.

No matter whether the implanted medical device is disposed outside or implanted into a body, the radiopaque structure may accord with the condition that in at least one incidence direction of a light source, at least one group of effective thickness $d_m$ and projection area $S_m$ of all radiopaque objects of the radiopaque structure accords with $S_m-0.0136(d_m)^a \geq 0-$, wherein a is more than or equal to $-0.95$ and less than or equal to $-0.85$.

It should be understood that the radiopaque structure on the implanted medical device may only include one radiopaque unit. In at least one incidence direction of the light source, at least one group of effective thickness $d_m$ and projection area $S_m$ of all radiopaque objects of the radiopaque unit accords with $S_m-0.0136(d_m)^a \geq 0$, wherein a is more than or equal to $-0.95$ and less than or equal to $-0.85$, so that the radiopaque structure in the implanted medical device has good or excellent visibility. Alternatively, the radiopaque structure on the implanted medical device also may include multiple mutually spaced radiopaque units. The effective thickness $d_m$ and the projection area $S_m$ of all the radiopaque objects of each radiopaque unit do not accord with the above characteristic relation, or the effective thickness $d_m$ of all the radiopaque objects of each radiopaque unit does not accord with the above characteristic relation, but in at least one incidence direction of the light source, the multiple mutually spaced radiopaque units have a radiopaque object overlapping portion, so that in this incidence direction, at least one group of effective thickness $d_m$ and projection area $S_m$ of all the radiopaque objects of a combination of the multiple radiopaque units accords with $S_m - 0.0136(d_m)^a \geq 0$, wherein a is more than or equal to −0.95 and less than or equal to −0.85, so that the radiopaque structure in the implanted medical device has good or excellent visibility. Alternatively, the radiopaque structure on the implanted medical device also may include multiple mutually spaced radiopaque units. The effective thickness $d_m$ and the projection area $S_m$ of all the radiopaque objects of each radiopaque unit do not accord with the above characteristic relation, and in at least one incidence direction of the light source, the multiple mutually spaced radiopaque units do not have the radiopaque object overlapping portion, but at least one group of effective thickness $d_m$ and projection area $S_m$ of all the radiopaque objects of a combination of the multiple radiopaque units accord with $S_m - 0.0136(d_m)^a \geq 0$, wherein a is more than or equal to −0.95 and less than or equal to −0.85, so that the radiopaque structure in the implanted medical device has good or excellent visibility.

In this present application, in order to better adapt to a small-sized implanted medical device and avoid influence on the mechanical property of the implanted medical device, the projection area $S_m$ of all the radiopaque objects of each radiopaque structure in the incidence direction is less than or equal to 1 mm², for example less than or equal to 0.5 mm².

In the present application, for example, in the incidence direction, the effective thickness $d_m$ of all the radiopaque objects of the radiopaque structure ranges from 0.02 mm to 0.24 mm.

Further, in the incidence direction, the effective thickness $d_m$ of all the radiopaque objects of the radiopaque structure ranges from 0.02 mm to 0.1 mm.

A further description will be made to the technical scheme of the present application in combination with specific embodiments and contrasts as follows. It should be noted that due to the precision limitation of a measuring instrument, the measurement precision of the projection areas of the radiopaque objects in the following embodiments shall include three decimal places, so that ($S_m$, $d_m$) in the following embodiments accord with $S_m - 0.0136(d_m)^a = 0$, including a situation that $S_m - 0.0136(d_m)^a$ infinitely approaches to 0 after ($S_m$, $d_m$) are substituted, and an absolute value of $S_m - 0.0136(d_m)^a$ herein is defined to be less than 1/1000, which is deemed to infinitely approach to 0. It should be understood that an image obtained by enabling $S_m - 0.0136(d_m)^a$ to infinitely approach to 0 and an image obtained under the condition of $S_m - 0.0136(d_m)^a = 0$ are undifferentiated under visual or eye identification.

Exemplary Embodiment 1

An iron-based alloy vascular stent includes a radiopaque structure. The radiopaque structure only includes one radiopaque unit which only includes an integral block-shaped radiopaque object. The stent includes multiple mutually spaced waveform ring-like objects, and any two adjacent waveform ring-like objects are connected through a connection member. A hole is formed in the connection member which is located at the proximal end of the stent, and is filled with the radiopaque object, thus the radiopaque structure is formed. The radiopaque object is only made of gold- and has a coverage area of 0.30 mm² in the circumferential direction of the stent. Under irradiation of an X-ray with an incidence direction approximately perpendicular to the coverage surface of the radiopaque object, the radiopaque object has a projection area of 0.268 mm², and the effective thickness corresponding to the projection area is 0.03 mm.

After the iron-based alloy vascular stent of this embodiment is implanted into a body, when the incidence direction of the X-ray is approximately perpendicular to the coverage surface of the radiopaque object, the radiopaque object of the radiopaque structure has at least one group of projection area and effective thickness ($S_m$, $d_m$)=(0.268, 0.03), which accords with $S_m - 0.0136(d_m)^{-0.85'} = 0$, so that an obtained image basically may be identified with eyes, namely the radiopaque structure has good visibility.

Exemplary Embodiment 2

An iron-based alloy vascular stent includes a radiopaque structure. The radiopaque structure only includes one radiopaque unit which includes four mutually spaced block-shaped radiopaque objects. The four mutually spaced radiopaque objects form an integral image under X-ray imaging equipment. The stent includes multiple mutually spaced waveform ringlike objects, and any two adjacent waveform ringlike objects are connected through a connection member. A hole is formed in the connection member which is located at the proximal end of the stent; and is filled with the radiopaque structure. The four radiopaque objects are only made of gold; and have a coverage area sum of 0.185 mm² in the circumferential direction of the stent. Under irradiation of an X-ray with an incidence direction approximately perpendicular to the coverage surfaces of the radiopaque objects, the four radiopaque objects have a projection area of about 0.165 mm², and the effective thickness corresponding to the projection area is 0.053 mm.

After the iron-based alloy vascular stent of this embodiment is implanted into a body, when the incidence direction of the X-ray is approximately perpendicular to the coverage surfaces of the radiopaque objects, the four radiopaque objects of the radiopaque structure have at least one group of projection area and effective thickness ($S_m$, $d_m$)=(0.165, 0.053), which accords with $S_m - 0.0136(d_m)^{-0.85'} = 0$, so that an obtained image basically may be identified with eyes, namely the radiopaque structure has good visibility.

Exemplary Embodiment 3

An iron-based alloy vascular stent includes a radiopaque structure. The radiopaque structure only includes one radiopaque unit which only includes an integral block-shaped radiopaque object. The stent includes multiple mutually spaced waveform ring-like objects, and any two adjacent waveform ringlike objects are connected through a connection member. A hole is formed in the connection member which is located at the proximal end of the stent, and is filled with the radiopaque object, thus the radiopaque structure is formed. The radiopaque object is only made of gold; and has a coverage area of 0.136 mm² in the circumferential direction of the stent. Under irradiation of an X-ray with an incidence direction approximately perpendicular to the coverage surface of the radiopaque object, the radiopaque object has a projection area of about 0.13 mm², and the effective thickness corresponding to the projection area is 0.07 mm.

After the iron-based alloy vascular stent of this embodiment is implanted into a body, when the incidence direction of the X-ray is approximately perpendicular to the coverage surface of the radiopaque object, the radiopaque object of the radiopaque structure has at least one group of projection area and effective thickness $(S_m, d_m)=(0.13, 0.07)$, which accords with $S_m - 0.0136(d_m)^{-0.85^\cdot} = 0$, so that an obtained image basically may be identified with eyes, namely the radiopaque structure has good visibility.

Exemplary Embodiment 4

An iron-based alloy vascular stent includes a radiopaque structure. The radiopaque structure only includes one radiopaque unit which only includes an integral block-shaped radiopaque object. The stent includes multiple mutually spaced waveform ring-like objects, and any two adjacent waveform ring-like objects are connected through a connection member. A hole is formed in the connection member which is located at the proximal end of the stent, and is filled with the radiopaque object, thus the radiopaque structure is formed. The radiopaque object is only made of gold; and has a coverage area of 0.101 mm² in the circumferential direction of the stent. Under irradiation of an X-ray with an incidence direction approximately perpendicular to the coverage surface of the radiopaque object, the radiopaque object has a projection area of about 0.096 mm², and the effective thickness corresponding to the projection area is 0.1 mm.

After the iron-based alloy vascular stent of this embodiment is implanted into a body, when the incidence direction of the X-ray is approximately perpendicular to the coverage surface of the radiopaque object, the radiopaque object of the radiopaque structure has at least one group of projection area and effective thickness $(S_m, d_m)=(0.096, 0.1)$, which accords with $S_m - 0.0136(d_m)^{-0.85^\cdot} = 0$, so that an obtained image basically may be identified with eyes, namely the radiopaque structure has good visibility.

Exemplary Embodiment 5

A magnesium-based alloy vascular stent includes a radiopaque structure. The radiopaque structure only includes one radiopaque unit which only includes an integral block-shaped radiopaque object. The stent includes multiple mutually spaced waveform ring-like objects, and any two adjacent waveform ring-like objects are connected through a connection member. A hole is formed in the connection member which is located at the proximal end of the stent, and is filled with the radiopaque object, thus the radiopaque structure is formed. The radiopaque object is only made of gold; and has a coverage area of 0.086 mm² in the circumferential direction of the stent. Under irradiation of an X-ray with an incidence direction approximately perpendicular to the coverage surface of the radiopaque object, the radiopaque object has a projection area of about 0.082 mm², and the effective thickness corresponding to the projection area is 0.12 mm.

After the magnesium-based alloy vascular stent of this embodiment is implanted into the body, when the incidence direction of the X-ray is approximately perpendicular to the coverage surface of the radiopaque object, the radiopaque object of the radiopaque structure has at least one group of projection area and effective thickness $(S_m, d_m)=(0.082, 0.12)$, which accords with $S_m - 0.0136(d_m)^{-0.85^\cdot} = 0$, so that an obtained image basically may be identified with eyes, namely the radiopaque structure has good visibility.

Exemplary Embodiment 6

A magnesium-based alloy vascular stent includes a radiopaque structure. The radiopaque structure only includes one radiopaque unit which only includes an integral block-shaped radiopaque object. The stent includes multiple mutually spaced waveform ring-like objects, and any two adjacent waveform ring-like objects are connected through a connection member. A hole is formed in the connection member which is located at the proximal end of the stent, and is filled with the radiopaque object, thus the radiopaque structure is formed. The radiopaque object is only made of gold- and has a coverage area of 0.0709 mm² in the circumferential direction of the stent. Under irradiation of an X-ray with an incidence direction approximately perpendicular to the coverage surface of the radiopaque object, the radiopaque object has a projection area of about 0.068 mm², and the effective thickness corresponding to the projection area is 0.15 mm.

After the magnesium-based alloy vascular stent of this embodiment is implanted into a body, when the incidence direction of the X-ray is approximately perpendicular to the coverage surface of the radiopaque object, the radiopaque object of the radiopaque structure has at least one group of projection area and effective thickness $(S_m, d_m)=(0.068, 0.15)$, which accords with $S_m - 0.0136(d_m)^{-0.85^\cdot} = 0$, so that an obtained image basically may be identified with eyes, namely the radiopaque structure has good visibility.

Exemplary Embodiment 7

An iron-based alloy vascular stent includes a radiopaque structure. The radiopaque structure only includes one radiopaque unit which includes four mutually spaced block-shaped radiopaque objects. The four mutually spaced radiopaque objects form an integral image under X-ray imaging equipment. The stent includes multiple mutually spaced waveform ringlike objects, and any two adjacent waveform ring-like objects are connected through a connection member. A hole is formed in the connection member which is located at the proximal end of the stent; and is filled with the radiopaque structure. The four radiopaque objects are only made of gold; and have a coverage area sum of 0.5 mm² in the circumferential direction of the stent. Under irradiation of an X-ray with an incidence direction approximately perpendicular to the coverage surfaces of the radiopaque objects, the four radiopaque objects have a projection area of about 0.43 mm², and the effective thickness corresponding to the projection area is 0.053 mm.

After the iron-based alloy vascular stent of this embodiment is implanted into a body, when the incidence direction of the X-ray is approximately perpendicular to the coverage surfaces of the radiopaque objects, the four radiopaque objects of the radiopaque structure have at least one group of projection area and effective thickness $(S_m, d_m)=(0.43, 0.053)$, which accords with $S_m - 0.0136(d_m)^{-0.85^\cdot} > 0$, so that an obtained image may be easily and clearly identified with eyes, namely the radiopaque structure has excellent visibility.

Exemplary Embodiment 8

An iron-based alloy vascular stent includes a radiopaque structure. The radiopaque structure only includes one radiopaque unit which only includes an integral block-shaped radiopaque object. The stent includes multiple mutually spaced waveform ring-like objects, and any two adjacent waveform ring-like objects are connected through a connection member. A hole is formed in the connection member which is located at the proximal end of the stent, and is filled with the radiopaque object, thus the radiopaque structure is formed. The radiopaque object is only made of gold; and has a coverage area of 0.35 mm² in the circumferential direction of the stent. Under irradiation of an X-ray with an incidence direction approximately perpendicular to the coverage surface of the radiopaque object, the radiopaque object has a projection area of about 0.3 mm², and the effective thickness corresponding to the projection area is 0.07 mm.

After the iron-based alloy vascular stent of this embodiment is implanted into a body, when the incidence direction of the X-ray is approximately perpendicular to the coverage surface of the radiopaque object, the radiopaque object of the radiopaque structure has at least one group of projection area and effective thickness $(S_m, d_m)=(0.3, 0.07)$, which accords with $S_m-0.0136(d_m)^{-0.85'}>0$, so that an obtained image may be easily and clearly identified with eyes, namely the radiopaque structure has excellent visibility.

Exemplary Embodiment 9

An absorbable polymer-based vascular stent includes a radiopaque structure. The radiopaque structure only includes one radiopaque unit which only includes an integral block-shaped radiopaque object. The stent includes multiple mutually spaced waveform ring-like objects, and any two adjacent waveform ring-like objects are connected through a connection member. A hole is formed in the connection member which is located at the proximal end of the stent, and is filled with the radiopaque object, thus the radiopaque structure is formed. The radiopaque object is only made of gold; and has a coverage area of 0.3 mm² in the circumferential direction of the stent. Under irradiation of an X-ray with an incidence direction approximately perpendicular to the coverage surface of the radiopaque object, the radiopaque object has a projection area of about 0.26 mm², and the effective thickness corresponding to the projection area is 0.2 mm.

After the absorbable polymer stent of this embodiment is implanted into a body, when the incidence direction of the X-ray is approximately perpendicular to the coverage surface of the radiopaque object, the radiopaque object of the radiopaque structure has at least one group of projection area and effective thickness $(S_m, d_m)=(0.26, 0.2)$, which accords with $S_m-0.0136(d_m)^{-0.85'}>0$, so that an obtained image may be easily and clearly identified with eyes, namely the radiopaque structure has excellent visibility.

Exemplary Embodiment 10

An iron-based alloy vascular stent includes a radiopaque structure. The radiopaque structure only includes one radiopaque unit which includes four mutually spaced block-shaped radiopaque objects. The four mutually spaced radiopaque objects form an integral image under X-ray imaging equipment. The stent includes multiple mutually spaced waveform ring-like objects, and any two adjacent waveform ring-like objects are connected through a connection member. Four holes are formed in the connection member which is located at the proximal end of the stent; and are respectively filled with the four radiopaque objects. The radiopaque objects are made of a mixture of gold powder and polylactic acid, wherein the volume fraction of gold is 66 percent. A total coverage area sum of the four radiopaque objects in the circumferential direction of the stent is 0.185 mm². Under irradiation of an X-ray with an incidence direction approximately perpendicular to the coverage surfaces of the radiopaque objects, the four radiopaque objects have a projection area of about 0.165 mm², and the average thickness of the radiopaque objects corresponding to the projection area is 0.08 mm, so that the effective thickness corresponding to the projection area is the product of the volume fraction of the gold and the average thickness of the radiopaque objects, and is 0.053.

After the iron-based alloy vascular stent of this embodiment is implanted into a body, when the X-ray is entering from the direction approximately perpendicular to the coverage surfaces of the radiopaque objects, the four radiopaque objects of the radiopaque structure have at least one group of projection area and effective thickness $(S_m, d_m)=(0.165, 0.053)$, which accords with $S_m-0.0136(d_m)^{-0.85'}=0$, so that an obtained image basically may be identified with eyes, namely the radiopaque structure has good visibility.

Exemplary Embodiment 11

An absorbable iron-based alloy vascular stent includes a radiopaque structure. The radiopaque structure includes two radiopaque units which are disposed at the proximal end of the stent and are staggered from each other by 180 degrees along the circumferential direction of the stent. Each radiopaque unit only includes an integral radiopaque object. The stent includes multiple mutually spaced waveform ring-like objects, and any two adjacent waveform ringlike objects are connected through a connection member. A hole is formed in each of two connection members which are disposed at the proximal end of the stent and are staggered from each other by 180 degrees along the circumferential direction of the stent, and is filled with each radiopaque object, thus the radiopaque structure is formed. The radiopaque objects are only made of gold, and the radiopaque object of each radiopaque unit has a coverage area of 0.135 mm² in the circumferential direction of the stent. Under irradiation of an X-ray with an incidence direction approximately perpendicular to the coverage surfaces of the radiopaque objects, the radiopaque objects of the two radiopaque units are completely overlapped, and have a projection area of about 0.092 mm², and the effective thickness corresponding to the projection area is 0.106 mm.

In this embodiment, when the X-ray is entering from the direction approximately perpendicular to the coverage surfaces of the radiopaque objects, the two radiopaque units have a radiopaque object overlapping region in the incidence direction of the X-ray; the two radiopaque objects of the radiopaque structure have at least one group of projection area and effective thickness $(S_m, d_m)=(0.092, 0.106)$, which accords with $S_m-0.0136(d_m)^{-0.85'}=0$, so that an obtained image may be identified with eyes, namely the radiopaque structure has good visibility.

Exemplary Embodiment 12

An iron-based alloy vascular stent includes a radiopaque structure. The radiopaque structure only includes one radiopaque unit which includes four mutually spaced block-shaped radiopaque objects. The four mutually spaced radiopaque objects form an integral image under X-ray imaging equipment. The stent includes multiple mutually spaced waveform ringlike objects, and any two adjacent waveform ringlike objects are connected through a connection member. A hole is formed in the connection member which is located at the proximal end of the stent; and is filled with the radiopaque structure. The four radiopaque objects are only made of gold; and have a coverage area sum of 0.23 $mm^2$ in the circumferential direction of the stent. Under irradiation of an X-ray with an incidence direction approximately perpendicular to the coverage surfaces of the radiopaque objects, the four radiopaque objects have a projection area of about 0.191 $mm^2$, and the effective thickness corresponding to the projection area is 0.053 mm.

After the iron-based alloy vascular stent of this embodiment is implanted into a body, when the incidence direction of the X-ray is approximately perpendicular to the coverage surfaces of the radiopaque objects, the four radiopaque objects of the radiopaque structure have at least one group of projection area and effective thickness $(S_m, d_m) = (0.191, 0.053)$, which accords with $S_m - 0.0136(d_m)^{-0.90°} = 0$, so that an obtained image basically may be identified with eyes, namely the radiopaque structure has good visibility.

Exemplary Embodiment 13

An iron-based alloy vascular stent includes a radiopaque structure. The radiopaque structure only includes one radiopaque unit which only includes an integral radiopaque object. The stent includes multiple mutually spaced waveform ring-like objects, and any two adjacent waveform ring-like objects are connected through a connection member. A hole is formed in the connection member which is located at the proximal end of the stent, and is filled with the radiopaque object, thus the radiopaque structure is formed. The radiopaque object is only made of gold; and has a coverage area of 0.20 $mm^2$ in the circumferential direction of the stent. Under irradiation of an X-ray with an incidence direction approximately perpendicular to the coverage surface of the radiopaque object, the radiopaque object has a projection area of 0.17 $mm^2$, and the effective thickness corresponding to the projection area is 0.07 mm.

After the iron-based alloy vascular stent of this embodiment is implanted into a body, when the incidence direction of the X-ray is approximately perpendicular to the coverage surface of the radiopaque object, the radiopaque object of the radiopaque structure has at least one group of projection area and effective thickness $(S_m, d_m) = (0.17, 0.07)$, which accords with $S_m - 0.0136(d_m)^{-0.95°} = 0$, so that an obtained image basically may be identified with eyes, namely the radiopaque structure has good visibility.

Exemplary Embodiment 14

Figure 3:
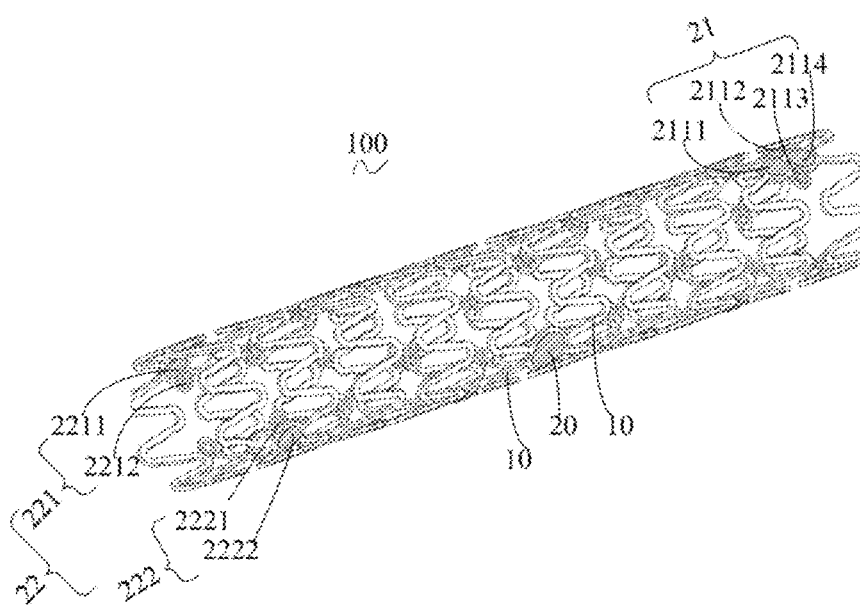
FIG. 3 is a schematic diagram of a structure of an iron-based alloy vascular stent of Embodiment 14 of the present application.

With reference to FIG. 3, an iron-based alloy vascular stent 100 includes multiple mutually spaced waveform ring-like objects 10, and any two adjacent waveform ring like objects are connected through a connection member (not marked in the figure). The iron-based alloy vascular stent 100 further includes a first radiopaque structure 20, a second radiopaque structure 21 and a third radiopaque structure 22 which are disposed on the connection members.

The first radiopaque structure 20 only includes one radiopaque unit (not marked in the figure) which only includes an integral radiopaque object (not marked in the figure). A hole is formed in the connection member at the middle section of the stent 100; and is filled with the radiopaque object of the first radiopaque structure 20, thus the first radiopaque structure 20 is formed. The radiopaque object is only made of gold; and has a coverage area of 0.136 $mm^2$ in the circumferential direction of the stent 100. Under irradiation of an X-ray with an incidence direction approximately perpendicular to the coverage surface of the radiopaque object, the radiopaque object has a projection area of about 0.13 $mm^2$, and the effective thickness corresponding to the projection area is 0.07 mm.

The second radiopaque structure 21 only includes one radiopaque unit (not marked in the figure) which includes four mutually spaced block-shaped radiopaque objects 2111, 2112, 2113 and 2114. The four mutually spaced radiopaque objects 2111, 2112, 2113 and 2114 form an integral image under X-ray imaging equipment. Four holes are formed in the connection member which is located at the proximal end of the stent 100; and are respectively filled with the four radiopaque objects 2111, 2112, 2113 and 2114. The four radiopaque objects are only made of gold; and have a coverage area sum of 0.185 $mm^2$ in the circumferential direction of the stent. Under irradiation of an X-ray with an incidence direction approximately perpendicular to the coverage surfaces of the radiopaque objects, the radiopaque objects have a projection area of about 0.165 $mm^2$, and the effective thickness corresponding to the projection area is 0.053 mm.

The third radiopaque structure 22 is disposed at the distal end of the stent 100; and includes a first radiopaque unit 221 and a second radiopaque unit 222. In this embodiment, the first radiopaque unit 221 and the second radiopaque unit 222 are staggered from each other by 180 degrees in the circumferential direction of the stent 100. The first radiopaque unit 221 includes a first radiopaque object 2211 and a second radiopaque object 2212 which are spaced from each other; two holes are formed in the connection member which is located at the proximal end of the stent 100; and are respectively filled with the first radiopaque object 2211 and a second radiopaque object 2212. The second radiopaque unit 222 includes a third radiopaque object 2221 and a fourth radiopaque object 2222 which are spaced from each other; two holes are formed in the connection member, which is staggered from the first radiopaque unit by 180 degrees, at the proximal end of the stent 100, and are filled with the third radiopaque object 2221 and the fourth radiopaque object 2222 respectively. The first, second, third and fourth radiopaque objects 2211, 2212, 2221 and 2222 form an integral image under X-ray imaging equipment, and are only made of gold, and a coverage area sum of the first, second, third and fourth radiopaque objects 2211, 2212, 2221 and 2222 in the circumferential direction of the stent 100 is 0.185 $mm^2$. Under irradiation of an X-ray with an incidence direction approximately perpendicular to the coverage surfaces of the radiopaque objects, there is no overlapping region between the radiopaque objects of the first radiopaque unit 221 and the second radiopaque unit 222; and the first, second, third and fourth radiopaque objects 2211, 2212, 2221 and 2222 have a projection area of about 0.165 $mm^2$, and the effective thickness corresponding to the projection area is 0.053 mm.

When the iron-based alloy vascular stent 100 of this embodiment is implanted into a body, and the incidence direction of the X-ray is approximately perpendicular to the coverage surface of the radiopaque object of the first radiopaque structure 20, the radiopaque object of the first radiopaque structure 20 has at least one group of projection area and effective thickness $(S_m, d_m) = (0.13, 0.07)$, which accords with $S_m - 0.0136(d_m)^{-0.85°} = 0$, so that an obtained image basically may be identified with eyes, namely the first radiopaque structure 20 has good visibility.

When the incidence direction of the X-ray is approximately perpendicular to the coverage surfaces of the radiopaque objects of the second radiopaque structure 21, the four radiopaque objects 2111, 2112, 2113 and 2114 of the second radiopaque structure 21 have at least one group of projection area and effective thickness $(S_m, d_m)=(0.165, 0.053)$, which accords with $S_m-0.0136(d_m)^{-0.85°}=0$, so that an obtained image basically may be identified with eyes, namely the second radiopaque structure 21 has good visibility.

When the incidence direction of the X-ray is approximately perpendicular to the coverage surfaces of the radiopaque objects of the third radiopaque structure 22, the first, second, third and fourth radiopaque objects 2211, 2212, 2221 and 2222 of the third radiopaque structure 22 have at least one group of projection area and effective thickness $(S_m, d_m)=(0.165, 0.053)$, which accords with $S_m-0.0136(d_m)^{-0.85°}=0$, so that an obtained image basically may be identified with eyes, namely the third radiopaque structure 22 has good visibility.

In this embodiment, the first radiopaque structure 20 and the first radiopaque unit 221 of the third radiopaque structure 22 are staggered from each other by 90 degrees in the circumferential direction of the stent 100. Therefore, information such as an axial length or a rotating angle of the stent 100 may be calculated according to images displayed under the imaging equipment due to the cooperation of the first radiopaque structure 20, the second radiopaque structure 21 and the third radiopaque structure 22.

It should be understood that the stent 100 also may include other radiopaque structures disposed on it, so that after the stent 100 is implanted in the body, at least one radiopaque structure may have good visibility under all incidence angles of an X-ray.

The embodiments of the present application are described above in combination with the drawings, but the present application is not limited to the above-mentioned specific implantation modes that are only schematic, not restrictive. Ordinary persons skilled in the art can make many implementation modes without departing from the idea of the present application and the scope claimed by claims under the inspiration of the present application, and these implementation modes shall all fall within the protection of the present application.

The invention claimed is:

1. A radiopaque structure, comprising:
   at least one radiopaque unit, wherein each radiopaque unit includes a number of radiopaque objects,
   wherein in at least one incidence direction of a light source each of the radiopaque objects has a region m, a projection area $S_m$ and an effective density $d_m$ according to $S_m-0.0136(d_m)^a \geq 0$,, wherein a is more than or equal to $-0.95$ and less than or equal to $-0.85$, so that the radiopaque structure is able to be viewed using imaging equipment after implantation into a human,
   wherein the effective thickness $d_m$ of a region m corresponds to an average thickness of the projection area $S_m$ of the region m, as defined by
   $d_m=(\Sigma_{i=1}^m S_i d_i)/S_m$
   in which:
      i is the number of radiopaque objects and is greater than 1,
      $d_i$ is a thickness for each of the i radiopaque objects in the at least one incidence direction, wherein the i radiopaque objects are divided into n regions according to the thickness $d_i$, n being more than or equal to 1, and n being 1 for i radiopaque objects with equal thicknesses $d_i$, and
      m is a number of regions randomly taken from the n regions, and m is more than or equal to 1, but less than or equal to n,
      $S_i$ is a projection area of each of the i radiopaque objects from the light source, and
      $S_m$ is a sum of the projection areas $S_i$ of the m regions.

2. The radiopaque structure according to claim 1, wherein a is equal to $-0.90$.

3. The radiopaque structure according to claim 1, wherein in the incidence direction, the effective thickness $d_m$ of the m regions of the n regions ranges from 0.02 mm to 0.24 mm.

4. The radiopaque structure according to claim 3, wherein in the incidence direction, the effective thickness $d_m$ of the m regions of the n regions ranges from 0.02 mm to 0.1 mm.

5. The radiopaque structure according to claim 1, wherein in the incidence direction, the projection area $S_m$ of the m regions of the n regions is less than or equal to 1 mm$^2$.

6. The radiopaque structure according to claim 5, wherein in the incidence direction, the projection area $S_m$ of the m regions of the n regions is less than or equal to 0.5 mm$^2$.

7. The radiopaque structure according to claim 1, wherein the structure comprises one radiopaque unit.

8. The radiopaque structure according to claim 1, wherein the radiopaque structure comprises multiple mutually spaced radiopaque units.

9. The radiopaque structure according to claim 1, wherein the radiopaque object is made of a radiopaque material, and the radiopaque material is selected from the group consisting of gold, platinum, osmium, rhenium, tungsten, iridium, rhodium, tantalum, barium sulfate, columbium sesquioxide, titanium oxide, zirconium oxide, elemental iodine and iodide.

10. The radiopaque structure according to claim 9, wherein when the radiopaque object comprises various radiopaque materials, and the average atomic number of a mixture of the various radiopaque materials is less than the atomic number of gold.

11. The radiopaque structure according to claim 1, wherein the radiopaque object comprises a radiopaque material and a non-radiopaque material, and the radiopaque material is selected the group consisting of gold, platinum, osmium, rhenium, tungsten, iridium, rhodium, tantalum, barium sulfate, columbium sesquioxide, titanium oxide, zirconium oxide, elemental iodine and iodide.

12. The radiopaque structure according to claim 11, wherein the non-radiopaque material is a degradable polymer material.

13. An implantable medical device, comprising a substrate and at least one radiopaque structure connected with the substrate,
   wherein the at least one radiopaque structure comprises at least one radiopaque unit,
   wherein each radiopaque unit includes at least one radiopaque object, and
   wherein in at least one incidence direction of a light source the at least one radiopaque object has a region m, a projection area $S_m$ and an effective thickness $d_m$ according to $S_m-0.0136(d_m)^a \geq 0$,, wherein a is more than or equal to $-0.95$ and less than or equal to $-0.85$, so that at least the at least one radiopaque structure provides an intact, continuous and independent image from the substrate using imaging equipment after implantation of the implantable medical device into a human, wherein the effective thickness $d_m$ of a region m corresponds to an average thickness of the projection area $S_m$ of the region m, as defined by
$d_m = (\Sigma_{i=1}^{m} S_i d_i)/S_m$
in which:
- i is the number of the at least one radiopaque object,
- $d_i$ is a thickness for each of the i radiopaque objects in the at least one incidence direction, wherein the i radiopaque objects are divided into n regions according to the thickness $d_i$, n being more than or equal to 1, and n being 1 for i radiopaque objects with equal thicknesses $d_i$, and
- m is a number of regions randomly taken from the n regions, and m is more than or equal to 1, but less than or equal to n,
- $S_i$ is a projection area of each of the i radiopaque objects from the light source, and
- $S_m$ is a sum of the projection areas $S_i$ of the m regions.

14. The implanted medical device according to claim 13, wherein multiple radiopaque units are provided, and the radiopaque objects of at least two radiopaque units have an overlapping region in the incidence direction.

15. The implanted medical device according to claim 13, wherein multiple radiopaque structures are provided, wherein at least one radiopaque structure comprises multiple mutually spaced radiopaque units, and each radiopaque unit in the radiopaque structure comprises multiple mutually spaced radiopaque objects; and at least another one radiopaque structure comprises one radiopaque unit which comprises multiple mutually spaced radiopaque objects.

16. The implanted medical device according to claim 13, wherein the substrate is one of a metal having a thickness less than or equal to 150 microns, or a polymer having a thickness less than or equal to 220 microns.

17. The implanted medical device according to claim 16, wherein the substrate is a magnesium-based alloy having a thickness less than or equal to 150 microns.

18. The implanted medical device according to claim 16, wherein the substrate is a zinc-based alloy having a thickness less than or equal to 100 microns.

19. The implanted medical device according to claim 16, wherein the substrate is an iron-based alloy having a thickness less than or equal to 70 microns.

20. A radiopaque structure, comprising:
at least one radiopaque unit, wherein each radiopaque unit includes at least one radiopaque object, wherein in at least one incidence direction of a light source the at least one radiopaque object has a region m, a projection area $S_m$ and an effective thickness $d_m$ according to $S_m - 0.0136(d_m)^a \geq 0$', wherein a is more than or equal to $-0.95$ and less than or equal to $-0.85$, so that the radiopaque structure is able to be viewed using imaging equipment after implantation into a human,
wherein the effective thickness $d_m$ of a region m corresponds to an average thickness of the projection area $S_m$ of the region m, as defined by
$d_m = (\Sigma_{i=1}^{m} S_i d_i)/S_m$
in which:
- i is the number of radiopaque objects and is greater than 1,
- $d_i$ is a thickness for each of the i radiopaque objects in the at least one incidence direction, wherein the i radiopaque objects are divided into n regions according to the thickness $d_i$, n being more than or equal to 1, and n being 1 for i radiopaque objects with equal thicknesses $d_i$, and
- m is a number of regions randomly taken from the n regions, and m is more than or equal to 1, but less than or equal to n,
- $S_i$ is a projection area of each of the i radiopaque objects from the light source, and
- $S_m$ is a sum of the projection areas $S_i$ of the m regions.

* * * * *